(12) United States Patent
Yao et al.

(10) Patent No.: US 11,627,911 B2
(45) Date of Patent: Apr. 18, 2023

(54) SYSTEM FOR EVALUATING SLEEPING COMFORT OF BEDDING SYSTEM

(71) Applicant: The Hong Kong Research Institute of Textiles and Apparel Limited, Hong Kong (CN)

(72) Inventors: Gloria Lei Yao, Hong Kong (CN); John Kin-ming Leung, Hong Kong (CN); Erika Kit-shan Ngan, Hong Kong (CN); Ryan Sai-yuk Leung, Hong Kong (CN); Siu-cheung Ho, Hong Kong (CN); Lv Ru, Hong Kong (CN); Hing-leung Chan, Hong Kong (CN); Jasmine Li Chi, Hong Kong (CN); Yammy Yan-yi Cheng, Hong Kong (CN); Christopher Wui-ka Ho, Hong Kong (CN); Venus Hoi-yan Lee, Hong Kong (CN); Cathy Hiu-ching Li, Hong Kong (CN)

(73) Assignee: The Hong Kong Research Institute of Textiles and Apparel Limited, Hong Kong (CN)

( * ) Notice: Subject to any disclaimer, the term of this patent is extended or adjusted under 35 U.S.C. 154(b) by 461 days.

(21) Appl. No.: 16/839,299

(22) Filed: Apr. 3, 2020

(65) Prior Publication Data
US 2021/0307680 A1 Oct. 7, 2021

(51) Int. Cl.
*A61B 5/00* (2006.01)
*A61G 7/057* (2006.01)

(52) U.S. Cl.
CPC ............ *A61B 5/4815* (2013.01); *A61B 5/445* (2013.01); *A61B 5/74* (2013.01); *A61G 7/057* (2013.01);
(Continued)

(58) Field of Classification Search
CPC .... A61B 2560/0242; A61B 2560/0431; A61B 2562/0219; A61B 2562/0249;
(Continued)

(56) References Cited

U.S. PATENT DOCUMENTS

| 10,314,407 B1 | 6/2019 | Main et al. |
| 2010/0100004 A1* | 4/2010 | van Someren ......... G16H 50/30 600/595 |

(Continued)

*Primary Examiner* — Rene T Towa
*Assistant Examiner* — Alexander H Connor
(74) *Attorney, Agent, or Firm* — S&F/WEHRW

(57) ABSTRACT

An evaluation system including a hardware system for collecting real-time data for evaluating sleeping comfort performance of a bedding system is disclosed. The hardware system includes a thermal and moisture comfort measurement system, a thermal and moisture comfort control system, a biomechanical comfort control system, and a biomechanical comfort measurement system. The evaluation system also includes a computational system having a processor and a tactile database, and a portable device. The computational system is configured to receive and process the real-time data from the hardware system, and is communicatively connected to the portable device for transmitting real-time data for evaluating the bedding system and adjusting the hardware system. A mobile application executable on the portable device is configured to collect subjective opinion of the sleeper using questionnaires, and the processor is configured to perform combined analysis of the subjective opinion and the real-time data of the bedding system.

17 Claims, 12 Drawing Sheets

(52) U.S. Cl.
CPC ..... *A61B 5/4566* (2013.01); *A61B 2560/0431* (2013.01); *A61B 2562/029* (2013.01); *A61B 2562/0219* (2013.01); *A61B 2562/0247* (2013.01); *A61B 2562/0271* (2013.01); *A61G 2210/70* (2013.01); *A61G 2210/90* (2013.01)

(58) Field of Classification Search
CPC ...... A61B 2562/0271; A61B 2562/029; A61B 5/1036; A61B 5/1127; A61B 5/445; A61B 5/4566; A61B 5/4815; A61B 5/7264; A61B 5/74; A61G 2210/70; A61G 2210/90; A61G 7/057; A61G 7/0507; G01D 21/02; G01M 99/001; G01N 33/0001
See application file for complete search history.

(56) References Cited

U.S. PATENT DOCUMENTS

| | | | |
|---|---|---|---|
| 2010/0268121 A1* | 10/2010 | Kilborn | A61B 5/412 |
| | | | 600/587 |
| 2010/0317930 A1* | 12/2010 | Oexman | A47C 31/123 |
| | | | 600/300 |
| 2011/0000018 A1* | 1/2011 | Kirchhoff | A47C 27/148 |
| | | | 219/490 |
| 2013/0281804 A1* | 10/2013 | Lee | A61G 7/057 |
| | | | 600/324 |
| 2014/0201922 A1* | 7/2014 | Sauser | A61G 7/0514 |
| | | | 5/689 |
| 2018/0027988 A1* | 2/2018 | Poodeh | G06T 7/73 |
| 2019/0376945 A1 | 12/2019 | Yao et al. | |
| 2020/0315367 A1* | 10/2020 | Demirli | A61B 5/1116 |

* cited by examiner

SYSTEM FOR EVALUATING SLEEPING COMFORT OF BEDDING SYSTEM

FIELD OF THE INVENTION

The present disclosure generally relates to the field of sleeping comfort evaluation of a bedding, and particularly relates to a hardware system and a software system for providing real-time sleeping comfort monitoring and making adjustment on the bedding microclimate, pressure distribution, and spinal support of a bedding system.

BACKGROUND OF THE INVENTION

Sleep plays a vital role in health and well-being of a person, and may affects the physical and mental health. People are paying more and more attention to sleeping comfort, and seeking bedding products with higher degree of comfort. It is generally agreed that a comfy and supportive mattress is essential for ensuring a good quality of sleep. Many factors affect the degree of sleeping comfort, such as, bedding microclimate, bedding pressure distribution, and spinal support, and tactile comfort of underwear. The evaluation is generally subjective and based on some unstandardized assessments.

Humans have a complex sensory system. Each part of the body, from the outer skin to the inner tissues and bones, has different sensitivities and requirements for temperature, humidity, pressure, and the material of the underclothing. The sleep environment and conditions affect a person's physiological and psychological reactions in the sleep. For example, the microclimate environment on the temperature and humidity of the textile or bedding in contact with the skin affects the feeling of comfort, the pressure distribution on the mattress surface affects the blood flow of the skin and tissues, and the support of the mattress affects the spine alignment and the stress on the spine. Therefore, the properties of the bedding with respect to the warmth, humidity, smoothness and hardness have an effect on the touch of the skin, thereby collectively affect the sleeping comfort and sleep quality of a person.

In the conventional system for evaluating the sleeping comfort, bedding can only be controlled and monitored on the temperature, humidity, pressure distribution, and spinal support individually. Some beds can be categorized as providing good support on the spine, but the pressure distribution and bedding microclimate are not evaluated. Therefore, the bed may only improve the sleeping quality and comfort of the user on one particular aspect or to certain extents only. Further, the conventional system cannot evaluate the touch comfort and cannot provide a comprehensive analysis on the sleeping environment.

Accordingly, there is a need in the art for a comprehensive system that seeks to address at least some of the above problems by evaluating and adjusting the bedding microclimate, pressure distribution, and spinal support of a mattress. Furthermore, other desirable features and characteristics will become apparent from the subsequent detailed description and the appended claims, taken in conjunction with the accompanying drawings and this background of the disclosure.

SUMMARY OF THE INVENTION

Provided herein is a hardware system and a software system for providing real-time sleeping comfort evaluation of a bedding. It is an objective of the present disclosure to provide a system that can provide real-time sleeping comfort monitoring and adjustment of bedding microclimate, pressure distribution, and spinal support of a mattress.

In accordance with certain embodiments of the present disclosure, an evaluation system for evaluating sleeping comfort performance of a bedding system is disclosed. The evaluation system includes a hardware system for collecting real-time data. The hardware system includes a thermal and moisture comfort measurement system, a thermal and moisture comfort control system, a biomechanical comfort control system, and a biomechanical comfort measurement system. The thermal and moisture comfort measurement system includes a plurality of first temperature sensors and a plurality of humidity sensors, each first temperature sensor is used for measuring a temperature of a position of a bedding, each humidity sensor is used for measuring a relative humidity of a position of the bedding. The thermal and moisture comfort control system is used for adjusting one or more bedding temperatures of the bedding and one or more bedding relative humidity of the bedding. The biomechanical comfort control system comprises a firmness-controllable mattress and a mattress firmness control machine, the firmness-controllable mattress comprises a plurality of firmness-controllable component mattresses, the mattress firmness control machine is used for adjusting firmness of each firmness-controllable component mattress such that pressure distribution on an interface between a sleeper and the firmness-controllable mattress and the spinal alignment of the sleeper are adjustable. The biomechanical comfort measurement system comprises a pressure sensing mat and a spinal alignment measurement device, the pressure sensing mat is located on the firmness-controllable mattress and comprises a plurality of pressure sensors, each pressure sensor is used for measuring pressure on a position of the interface such that the pressure distribution on the interface is obtained based on the measured pressure, a spinal alignment measurement device is used for measuring one or more spinal alignment parameters of the sleeper.

Preferably, the thermal and moisture comfort measurement system further comprises a second temperature sensor and a second humidity sensor, the second temperature sensor being used for measuring an ambient temperature, the second humidity sensor being used for measuring an ambient relative humidity.

Preferably, the thermal and moisture comfort measurement system further comprises a plurality of third temperature sensors, each third temperature sensor being used for measuring a skin temperature of a part of the sleeper.

Preferably, the spinal alignment measurement device comprises a laser liner and a plurality of stickers, the plurality of stickers being used for being attached on a back of the sleeper, the laser liner being used for detecting a position of each sticker.

Preferably, the spinal alignment measurement device comprises a camera for capturing images of the back of the sleeper.

Preferably, the one or more spinal alignment parameters include a deviation area of a back of the sleeper, a deviation angle of the back and/or a deviation distance of the back.

In accordance with certain embodiments of the present disclosure, the evaluation system further comprises a bed. The firmness-controllable mattress is located on the bed; and the thermal and moisture comfort control system comprises a temperature and humidity regulator, a blower, a tube and a plurality of diffuser plates, the tube connecting the temperature and humidity regulator and the blower, the blower being used for generating an airflow to the bed via the plurality of diffuser plates, the temperature and humidity regulator being used for adjusting a temperature of the air flow and a relative humidity of the air flow such that the one or more bedding temperatures and the one or more bedding relative humidity are adjusted.

Preferably, the bedding has a plurality of microclimate controllable zones, the bedding temperature and the bedding relative humidity in each microclimate controllable zone are adjusted individually by the thermal and moisture comfort control system.

Preferably, each firmness-controllable component mattress comprises a bag; and the mattress firmness control machine comprises a pump for pumping air or a liquid into or out of the bag of each firmness-controllable component mattress.

Preferably, the plurality of firmness-controllable component mattresses has three firmness-controllable component mattresses, five firmness-controllable component mattresses or seven firmness-controllable component mattresses.

Preferably, the hardware system further comprises a polysomnography system for measuring one or more physiological parameters of the sleeper.

Preferably, the hardware system further comprises an acceleration sensor for determining position changes of the sleeper.

In accordance with certain embodiments of the present disclosure, the evaluation system further comprises a computational system having a processor and a tactile database, and a portable device. The computational system is configured to receive and process the real-time data from the hardware system, and is communicatively connected to the portable device for transmitting real-time data for evaluating the bedding system and adjusting the hardware system. The mobile application executable on the portable device is configured to collect subjective opinion of the sleeper using a plurality of questionnaires. The processor is configured to perform combined analysis of the subjective opinion and the real-time data of the bedding system, and send instructions to the hardware system to control the thermal and moisture comfort control system for adjusting the one or more bedding temperature of the bedding and the one or more bedding relative humidity; and control the mattress firmness control machine for adjusting the firmness of each firmness-controllable component mattress.

Preferably, the plurality of questionnaires comprises a Pittsburgh Sleep Quality Index (PSQI) questionnaire, a microclimate psychological questionnaire, a pressure distribution and spinal support assessment questionnaire, and a fabric tactile psychological questionnaire.

Preferably, the tactile database comprises data and information in relation to objective mechanical test results of bed fabrics for evaluating a touch comfort of the bed fabrics of the bedding.

Preferably, the objective mechanical test results comprise thermal conductivity, heat flux, bending stiffness, bending work, surface roughness, and surface friction of the bed fabrics.

Preferably, the processor is configured to use regression analysis to model a relationship between the objective mechanical test results of the bed fabrics and the subjective opinion.

In accordance with certain embodiments of the present disclosure, the evaluation system further comprises a cloud system comprising a cloud processor and a Big Data database of bed fabrics. The Big Data database stores a collection of mechanical test results of the bed fabrics and the subjective opinions of the bed fabrics. The subjective opinions are categorized according to personal demographic information enabling an extraction of relevant information from the Big Data database.

Preferably, the processor is further configured to control the thermal and moisture comfort control system based on real-time data measured by thermal and moisture comfort measurement system, and control the biomechanical comfort control system based on real-time data measured by the biomechanical comfort measurement system.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects and advantages of the present invention are disclosed as illustrated by the embodiments hereinafter.

BRIEF DESCRIPTION OF THE DRAWINGS

The appended drawings contain figures to further illustrate and clarify the above and other aspects, advantages, and features of the present disclosure. It will be appreciated that these drawings depict only certain embodiments of the present disclosure and are not intended to limit its scope. It will also be appreciated that these drawings are illustrated for simplicity and clarity and have not necessarily been depicted to scale. The present disclosure will now be described and explained with additional specificity and detail through the use of the accompanying drawings in which.

DETAILED DESCRIPTION OF THE INVENTION

Figure 1:
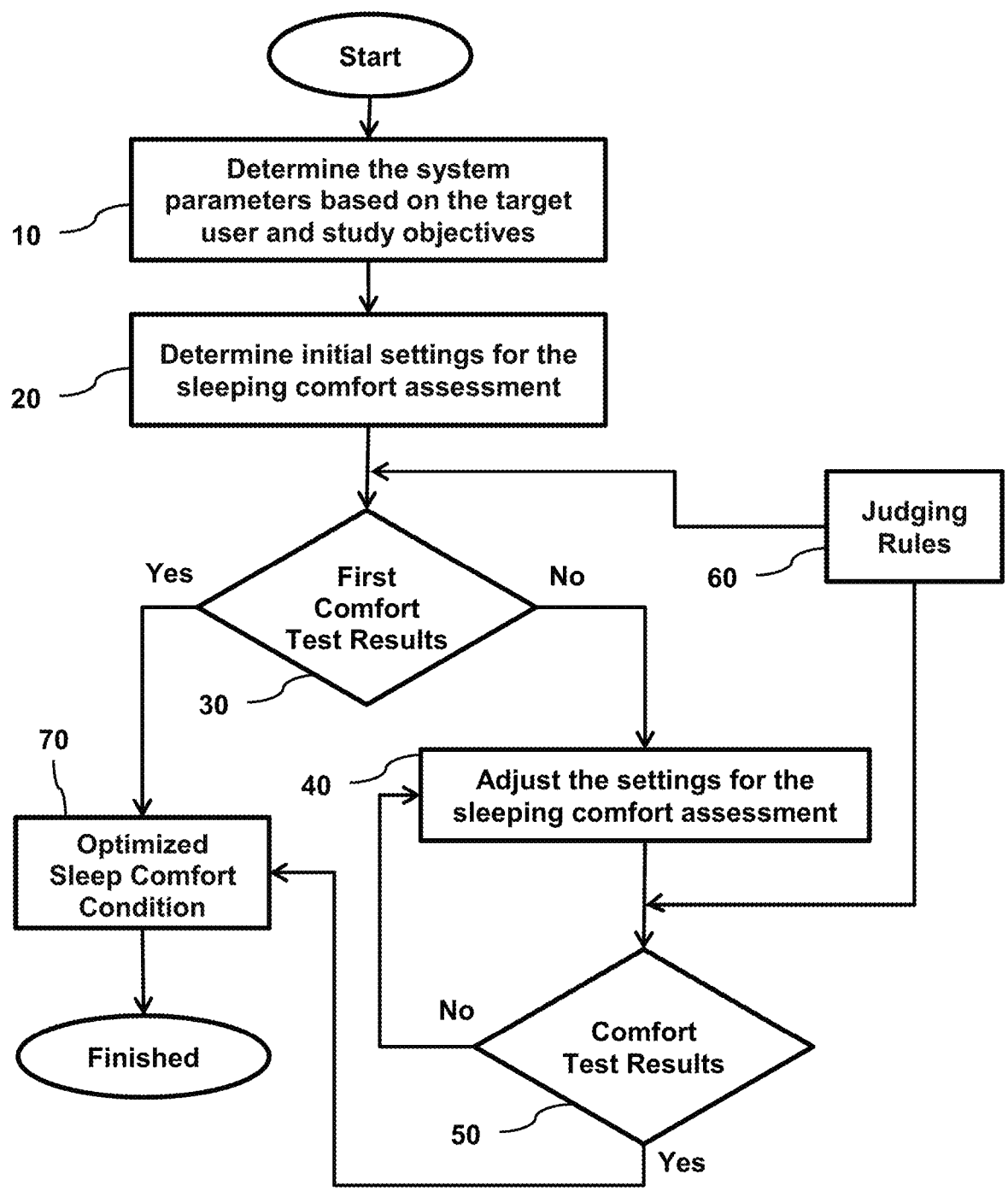
FIG. 1 depicts a flow diagram illustrating the sleeping comfort evaluation system according to certain embodiments.

The present disclosure generally relates to a hardware system and a software system for providing real-time sleeping comfort evaluation of a bedding. More specifically, but without limitation, the present disclosure provides a hardware system and a software system for performing real-time sleeping comfort monitoring and making adjustment on the bedding microclimate, pressure distribution, and spinal support of a mattress.

The following detailed description is merely exemplary in nature and is not intended to limit the disclosure or its application and/or uses. It should be appreciated that a vast number of variations exist. The detailed description will enable those of ordinary skilled in the art to implement an exemplary embodiment of the present disclosure without undue experimentation, and it is understood that various changes or modifications may be made in the function and structure described in the exemplary embodiment without departing from the scope of the present disclosure as set forth in the appended claims.

The benefits, advantages, solutions to problems, and any element(s) that may cause any benefit, advantage, or solution to occur or become more pronounced are not to be construed as a critical, required, or essential features or elements of any or all of the claims. The invention is defined solely by the appended claims including any amendments made during the pendency of this application and all equivalents of those claims as issued.

As used herein, the term "bedding system" refers to mattress, bedspread, pillow, pillow cover, blanket or quilt, and all other means adapted to be used for the sleeping environment, which may also include other articles used in baby cots, convertible beds, or outdoor beddings. It also includes the devices/software to adjust and manage the mattress firmness and bed microclimate. As used herein, the term "bedding" is defined as items normally placed on a mattress, e.g. mattress covers, underlays, sheets, blankets, quilts (duvets) and their covers, cushions, pillows, bolsters and pillow cases.

The term "cloud" is construed and interpreted in the sense of cloud computing or, synonymously, distributed computing over a network unless otherwise specified. "A server" as used herein is interpreted in the sense of computing. The one or more "database" may be, for example, electrical circuits, hard disks and/or other solid-state disks for storing data. Generally, a server is equipped with one or more processors for executing program instructions, and one or more storages for storing data. The server may be a standalone computing server or a distributed server in the cloud.

The term "Big Data" is generally used to describe collections of data of a relatively large size and complexity, such that the data becomes difficult to analyze and process within a reasonable time, given computational capacity (e.g., available database management tools and processing power). Thus, the term "Big Data" can refer to data collections measured in gigabytes, terabytes, or larger, depending on the processing entity's ability to handle the data. "Big Data" is intended to refer to collections of electronic data stored in one or more storage locations, and it is not intended to limit the applicability of the inventive subject matter to a particular data size range or a particular amount of data complexity.

FIG. 1 is a flow diagram illustrating the sleeping comfort evaluation system, which is aimed at identifying the optimized sleeping comfort condition. The present disclosure provides a measurement and evaluation system based on a hardware system and/or a software system for evaluating the sleeping comfort performance of a bedding system. The evaluation system is based on both objective parameters and subjective criteria. The objective parameters are measurable and quantitative information, including the bedding microclimate (both thermal and humidity comfort), pressure distribution, and biomechanical comfort. The subjective criteria are focused on the evaluation on the touch comfort of the bedding textiles.

The evaluation model is configured to first determine the system parameters based on the target user and study objectives 10, and determine the initial settings for a sleeping comfort assessment 20. This model is intended to be used by the mattress shops, product developers of the bedding system, and individual users having special or medical needs. The initial settings and the judging rules 60 for each parameter may be defined by the user of the evaluation model, based on average data in a database, or based on particular objective of the assessment. The judging rules 60 set the preferred limits for an acceptable and preferred result. When the conditions and settings are defined, the first assessment is executed to obtain the first comfort test results 30. If the result is within the preferred range as defined by the judging rules 60, the settings for the sleeping comfort assessment is the optimized sleep comfort condition 70. If any of the result is outside the preferred range, the corresponding or other relevant settings are adjusted for the sleeping comfort assessment 40. Based on the same judging rules 60, the assessment is executed again and another comfort test result 50 is obtained. If the result is within the preferred range as defined by the judging rules 60, the settings for the sleeping comfort assessment is the optimized sleep comfort condition 70. The iteration of adjusting the settings and executing the assessment is repeated until an optimized sleep comfort condition 70 is obtained.

Figure 2:
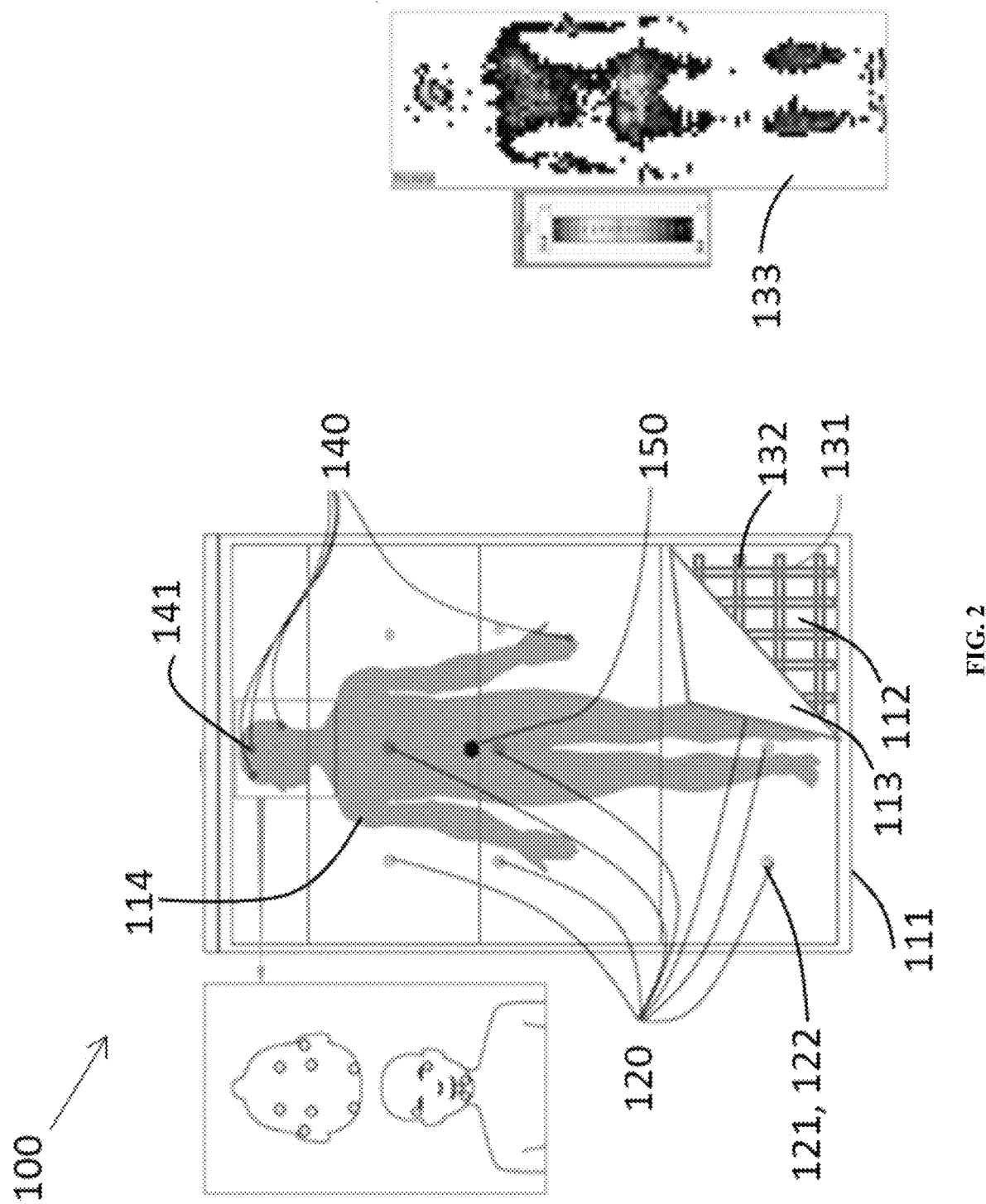
FIG. 2 depicts a hardware system of an evaluation system for evaluating sleeping comfort performance of a bedding system according to certain embodiments.

FIG. 2 depicts a hardware system of an evaluation system for evaluating sleeping comfort performance of a bedding system according to certain embodiments. The hardware system 100 comprises a bed 111, a firmness-controllable mattress 112, a bedding 113, a thermal and moisture comfort measurement system 120, a biomechanical comfort measurement system comprising a pressure sensing mat 131, a thermal and moisture comfort control system (not shown in FIG. 2), a biomechanical comfort control system (not shown in FIG. 2), a polysomnography system 140, an acceleration sensor 150.

The firmness-controllable mattress 112 is located above the bed 111. The bedding 113 is located on the firmness-controllable mattress 112. The thermal and moisture comfort measurement system 120 comprises temperature sensors 121 and humidity sensors 122. Some of the temperature sensors 121 are located on different positions of the bedding 113 and measure the temperatures at the different positions of the bedding 113 respectively. Some of the temperature sensors 121 are located on the skin of a sleeper 114 to measure skin temperature. Some of the temperature sensors 121 measure an ambient temperature. The humidity sensors 122 are located on different positions of the bedding 113 and measure the relative humidity at the different positions of the bedding 113 respectively.

The biomechanical comfort measurement system includes the pressure sensing mat 131. The pressure sensing mat 131 is located between the firmness-controllable mattress 112 and the bedding 113 and comprises pressure sensors 132 located on different positions of the pressure sensing mat 131. The pressure sensors 132 measure pressure on different positions of an interface between the sleeper 114 and the firmness-controllable mattress 112 respectively for determining an interface pressure distribution as shown in an image of a pressure distribution map 133.

The polysomnography system 140 comprises a plurality of sensors 141 for measuring sleep quality related physiological characteristics, e.g., brain wave, eye movement, etc. The acceleration sensor 150 measures a position change and an activity amount of the sleeper 114.

Figure 3:
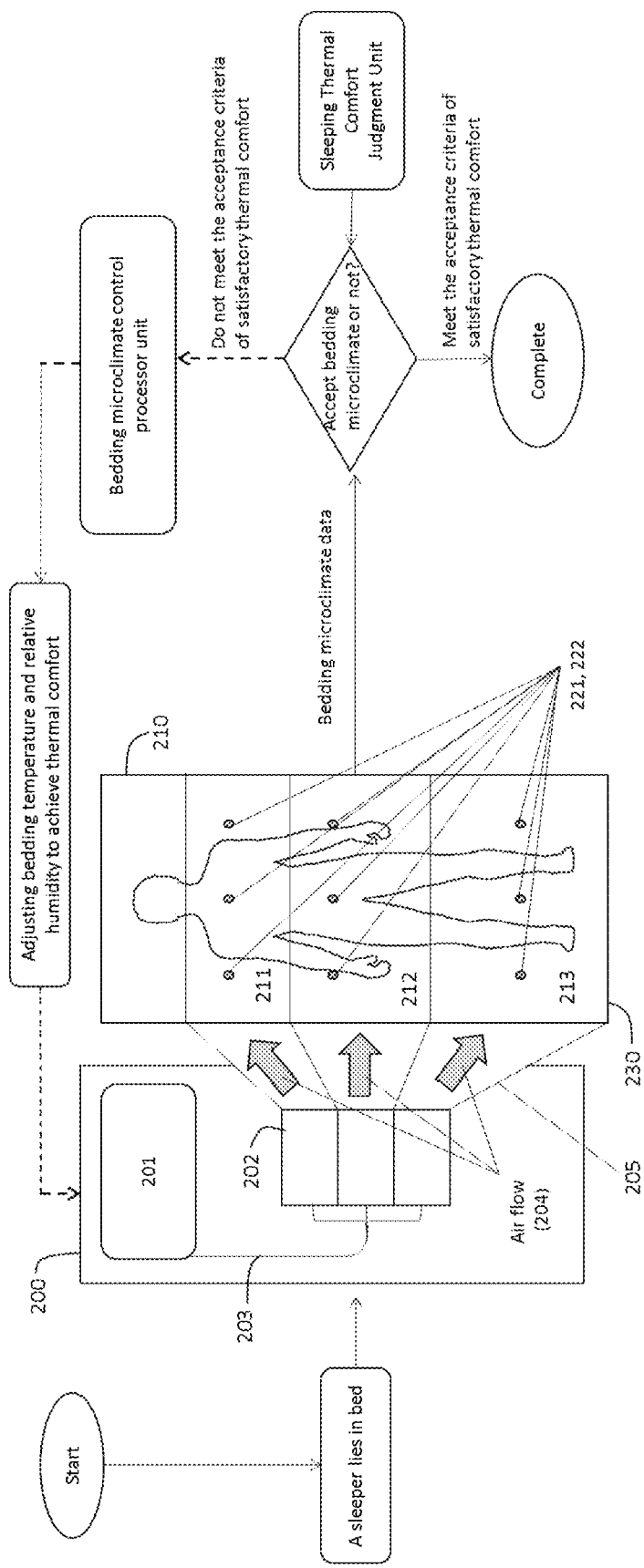
FIG. 3 depicts a thermal and moisture comfort control system according to certain embodiments.

FIG. 3 depicts a thermal and moisture comfort control system according to certain embodiments. The thermal and moisture comfort control system 200 adjusts a bedding temperature and a bedding relative humidity of a bedding 210 at different zones and comprises a temperature and humidity regulator 201, a blower 202, and a tube 203. The bedding 210 includes three microclimate controllable zones 211, 212, 213. Temperature sensors 221 and humidity sensors 222 are located on the three microclimate comfort zones 211, 212, 213 respectively. The temperature and humidity regulator 201 and the blower 202 are connected by the tube 203. The blower 202 generates air flow 204. The temperature and humidity regulator 201 regulates the temperature and the relative humidity of the air flow 204. The different amounts of the regulated air flow 204 are delivered to the bed 230 via diffuser plates 205 for adjusting the bedding temperature and the bedding relative humidity in the three microclimate controllable zones 211, 212, 213 respectively. In certain embodiments, temperature and humidity sensors are arranged at the air outlet and connected to a controller for providing feedback for automatic adjustment of the temperature and humidity of the air flow.

In this embodiment, the bedding microclimate data collected from the temperature sensors 221 and the humidity sensors 222 are analyzed to determine whether a bedding microclimate of the bedding 210 is accepted or not by a sleeping thermal comfort control judgment unit. If the bedding microclimate does not meet the acceptance criteria of satisfactory thermal and humidity comfort, a bedding microclimate control processor unit controls the thermal and moisture comfort control system 200 to adjust the bedding temperature and the bedding relative humidity in the three microclimate comfort zones 211, 212, 213 by delivering different amounts of the regulated air flow 204 into the three microclimate comfort zones 211, 212, 213.

In certain embodiments, the bedding has three microclimate controllable zones, five microclimate controllable zones, or seven microclimate controllable zones.

Figure 4:
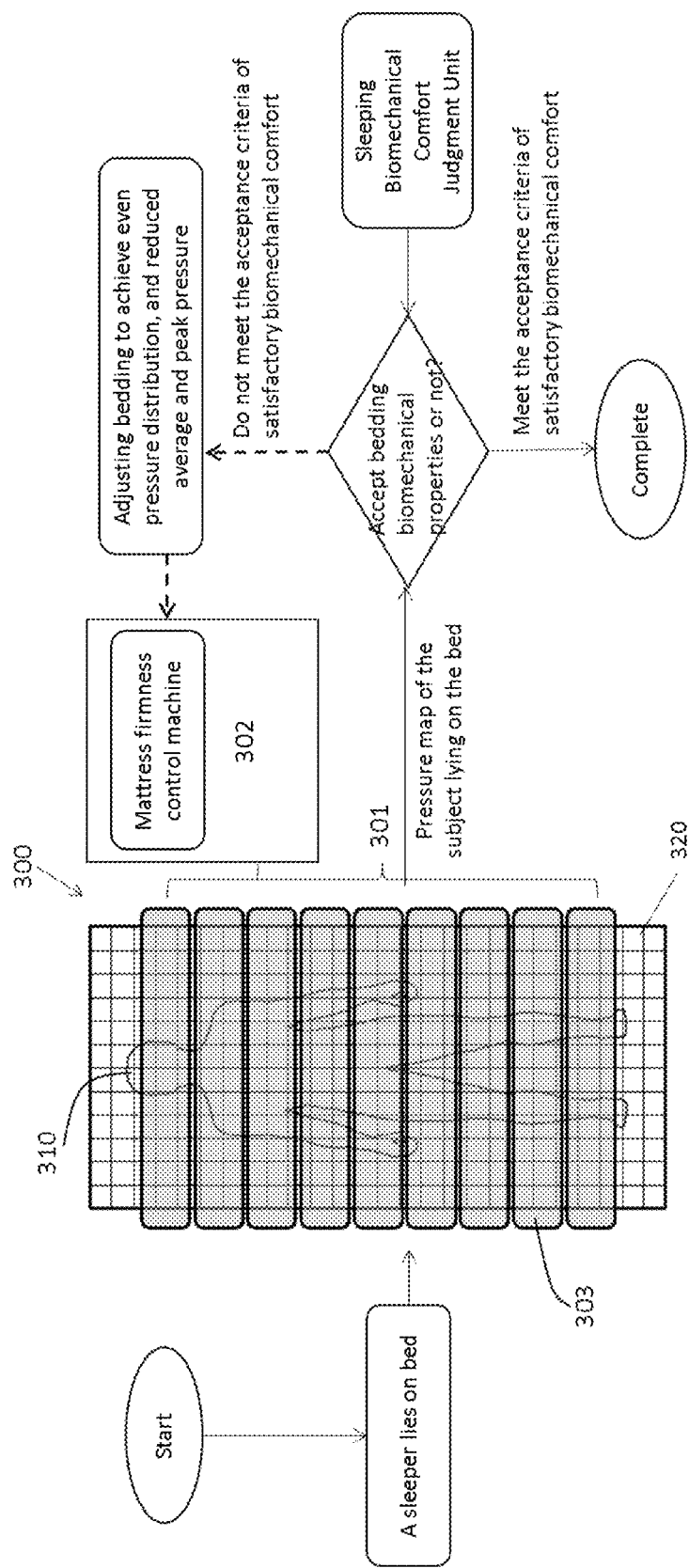
FIG. 4 depicts a biomechanical comfort control system according to certain embodiments.

FIG. 4 depicts a biomechanical comfort control system according to certain embodiments. The biomechanical comfort control system 300 comprises a firmness-controllable mattress 301 and a mattress firmness control machine 302. The firmness-controllable mattress 301 comprises a plurality of firmness-controllable component mattresses 303. Each firmness-controllable component mattress 303 is controlled by the mattress firmness control machine 302 individually.

In this embodiment, a pressure distribution map of a sleeper 310 lying on the firmness-controllable mattress 301 based on data collected from the pressure sensing mat 320 is analyzed by a bedding biomechanical comfort judgment unit to determine whether the existing bedding biomechanical properties are accepted or not. If the existing bedding biomechanical properties do not meet the acceptance criteria of the satisfactory biomechanical comfort, a bedding biomechanical control processor unit controls the mattress firmness control machine 302 to adjust the firmness-controllable mattress 301 to achieve even pressure distribution and/or reduce average pressure and peak pressure until the acceptance criteria of the satisfactory biomechanical comfort are met.

Figure 5:
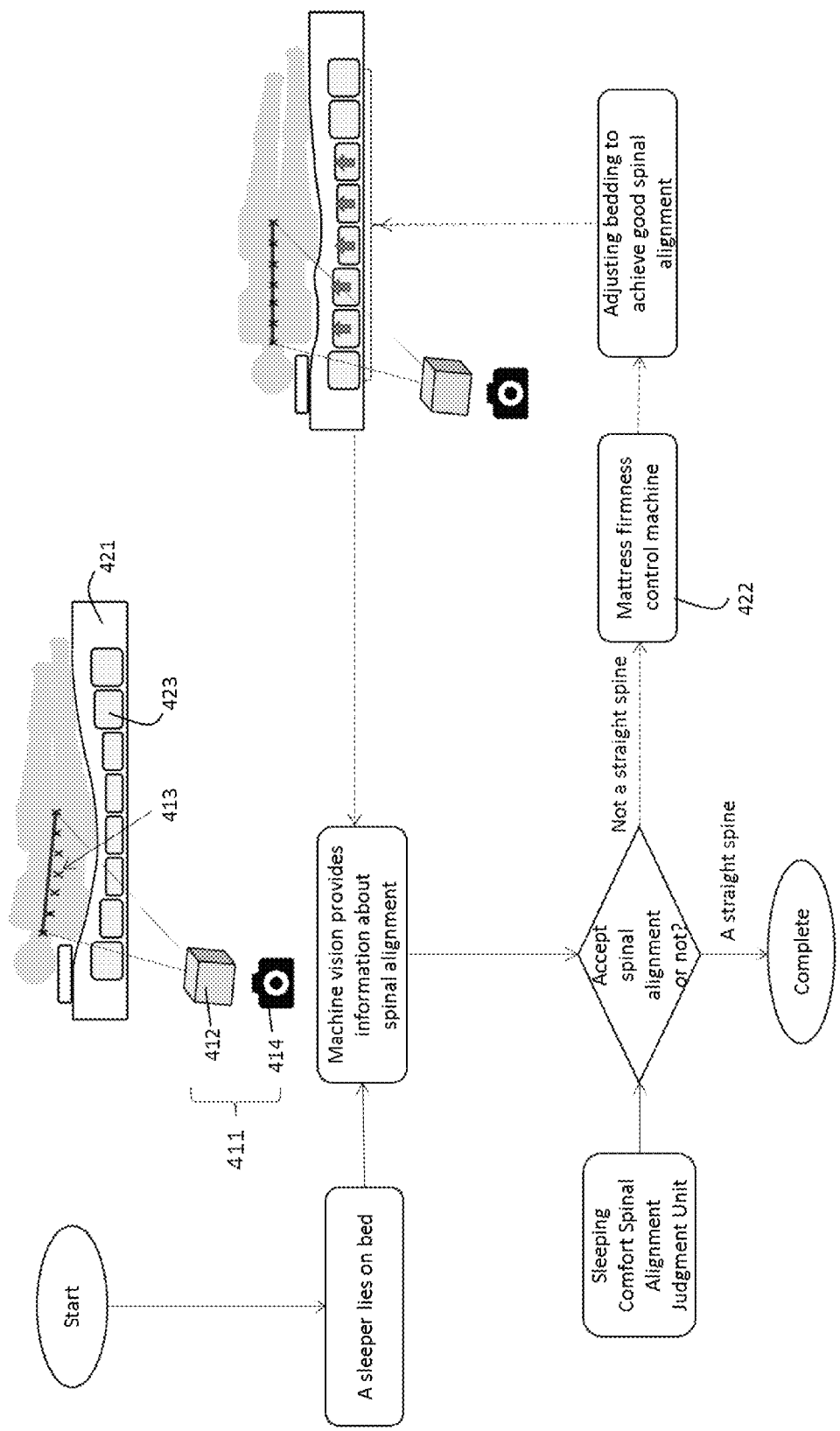
FIG. 5 depicts a spinal alignment measurement device and a spinal alignment control machine according to certain embodiments.

FIG. 5 depicts a spinal alignment measurement device and a spinal alignment control machine according to certain embodiments. The spinal alignment measurement device comprises a machine vision device 411 for obtaining information about spinal alignment. In this embodiment, the machine vision device 411 comprises a laser liner 412 for forming a virtual straight spine and stickers 413 attached on the back of the sleeper to local his spine. Alternatively, the machine vision device 411 is a camera 414 for capturing an image of the back of the sleeper.

The information about the spinal alignment is analyzed by a sleeping comfort spinal alignment judgment unit to determine whether the existing spinal alignment is accepted or not. If not, a spinal alignment control machine controls the spinal alignment of the sleeper. The spinal alignment control machine comprises a firmness-controllable mattress 421 and a mattress firmness control machine 422. The firmness-controllable mattress 421 comprises a plurality of firmness-controllable component mattress 423. The mattress firmness control machine 422 controls firmness-controllable mattress 421 to adjust the firmness of each firmness-controllable component mattress 423 individually to achieve good spinal alignment. Once a straight spine of the sleeper is obtained, the control of the spinal alignment is stopped.

In certain embodiments, the spinal alignment parameters include a deviation area, a deviation angle and/or a deviation distance.

In certain embodiments, each firmness-controllable component mattress comprises an air bag; and the mattress firmness control machine comprises a pump for pumping air into and out of the air bag of each firmness-controllable component mattress. In certain embodiment, each firmness-controllable component mattress comprises a liquid bag; and the mattress firmness control machine comprises a pump for pumping a liquid into and out of the liquid bag of each firmness-controllable component mattress. In certain embodiment, the firmness adjustment of the firmness-controllable component mattress is made by replacing a comfort layer or a support layer of the firmness-controllable component mattress with different firmness, or adding or removing firmness inserts in the firmness-controllable component mattress.

In certain embodiments, the firmness-controllable mattress has three firmness-controllable component mattresses, five firmness-controllable component mattresses or seven firmness-controllable component mattresses.

The evaluation system also includes a software system for providing real-time evaluation on the sleeping comfort performance of a bedding system. The software system is configured to make adjustment on the bedding microclimate (both thermal and humidity comfort), pressure distribution, and biomechanical comfort of a bedding system. The software system is based on an assessment on both the objective parameters and subjective criteria, and utilizes the hardware system 100 to perform the evaluation.

Figure 6:
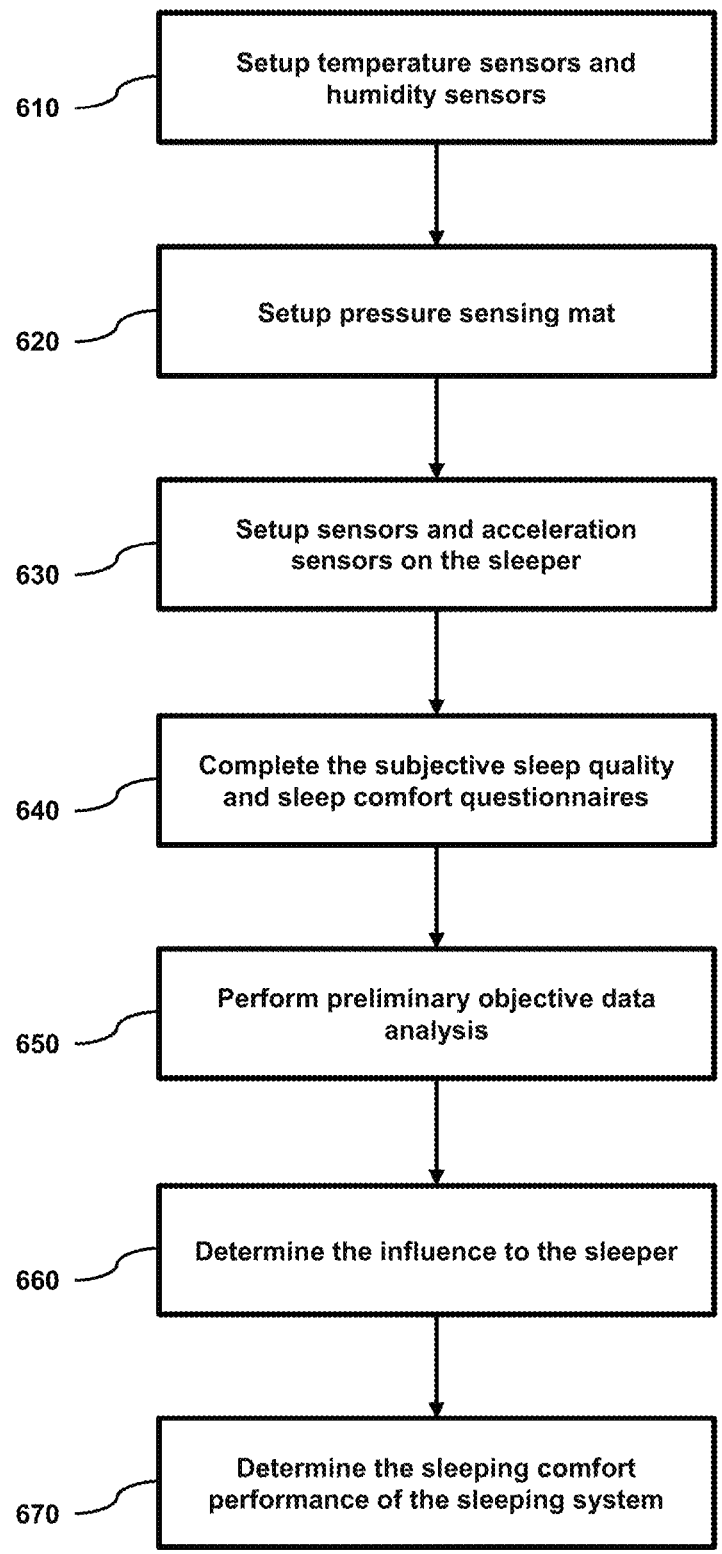
FIG. 6 depicts the method for performing evaluation on the sleeping comfort performance according to certain embodiments.

As shown in FIG. 6, the method for performing the evaluation on the sleeping comfort performance is depicted. The first step 610 is to setup a plurality of temperature sensors and a plurality of humidity sensors. The plurality of temperature sensors are used for measuring temperature of a plurality of positions of the bedding, and the plurality of humidity sensors are used for measuring the relative humidity of a plurality of positions of the bedding. The respective body temperature and humidity condition of the sleeper are also measured. The temperature and humidity are generally considered as the bedding microclimate, which are to be adjusted.

The second step 620 is to setup a pressure sensing mat and a spinal alignment measurement device. The pressure sensing mat is located on a firmness controllable mattress. Preferably, the pressure sensing mat includes a plurality of pressure sensors configured to measure the pressure on a plurality of positions of an interface between a sleeper and the firmness controllable mattress. The spinal alignment measurement device includes a machine vision device for obtaining information about spinal alignment by capturing an image of the back of the sleeper.

The third step 630 is to attach a plurality of sensors and acceleration sensors on the sleeper. The plurality of sensors of the polysomnography system and acceleration sensors are configured to measure the sleep quality of the sleeper, such as brain wave, eye movement, body position, and an activity amount of the sleeper.

The fourth step 640 requires the sleeper to complete the subjective sleep quality and sleep comfort questionnaires ("questionnaires") within a predetermined time. The questionnaires 732 (shown in FIG. 7) are used to assess the subjective opinion of the sleeper on the thermal and moisture comfort, biomechanical comfort, touch comfort, and sleep quality. The predetermined time may be within one day such that the questionnaires 732 can accurately capture the subjective opinion of the sleeper without mingling with the memory and feeling of another sleep. In certain embodiments, the questionnaires 732 includes the Pittsburgh Sleep Quality Index (PSQI) questionnaire 741, a microclimate psychological questionnaire 742, a pressure distribution and spinal support assessment questionnaire 743, and a fabric tactile psychological questionnaire 744, as shown in FIG. 8.

The fifth step 650 is to perform preliminary objective data analysis based on the hardware and software system to determine the performance of the bedding system. The data collected from the temperature sensors, the humidity sensors, the pressure sensors, the spinal alignment measurement device, the sensors of the polysomnography system, and the acceleration sensor are processed by a computational system. The data analysis can determine the bedding microclimate (thermal and moisture comfort), bedding pressure distribution, spinal support, and touch comfort of the bedding system.

The sixth step 660 is to compare the result from the preliminary data analysis with the sleep quality and sleep comfort questionnaires, thereby determines the influence to the sleeper with respects to the bedding microclimate (thermal and moisture comfort), bedding pressure distribution, and spinal support, and touch comfort.

The seventh step 670 is to determine the sleeping comfort performance of the bedding system. By relating the subjective parameters from the questionnaires with the objective parameters from the preliminary data analysis, in-depth evaluation of the performance of the bedding system can be performed. In particular, the bedding microclimate (thermal and moisture comfort), bedding pressure distribution, and spinal support, and touch comfort can be determined.

Figure 7:
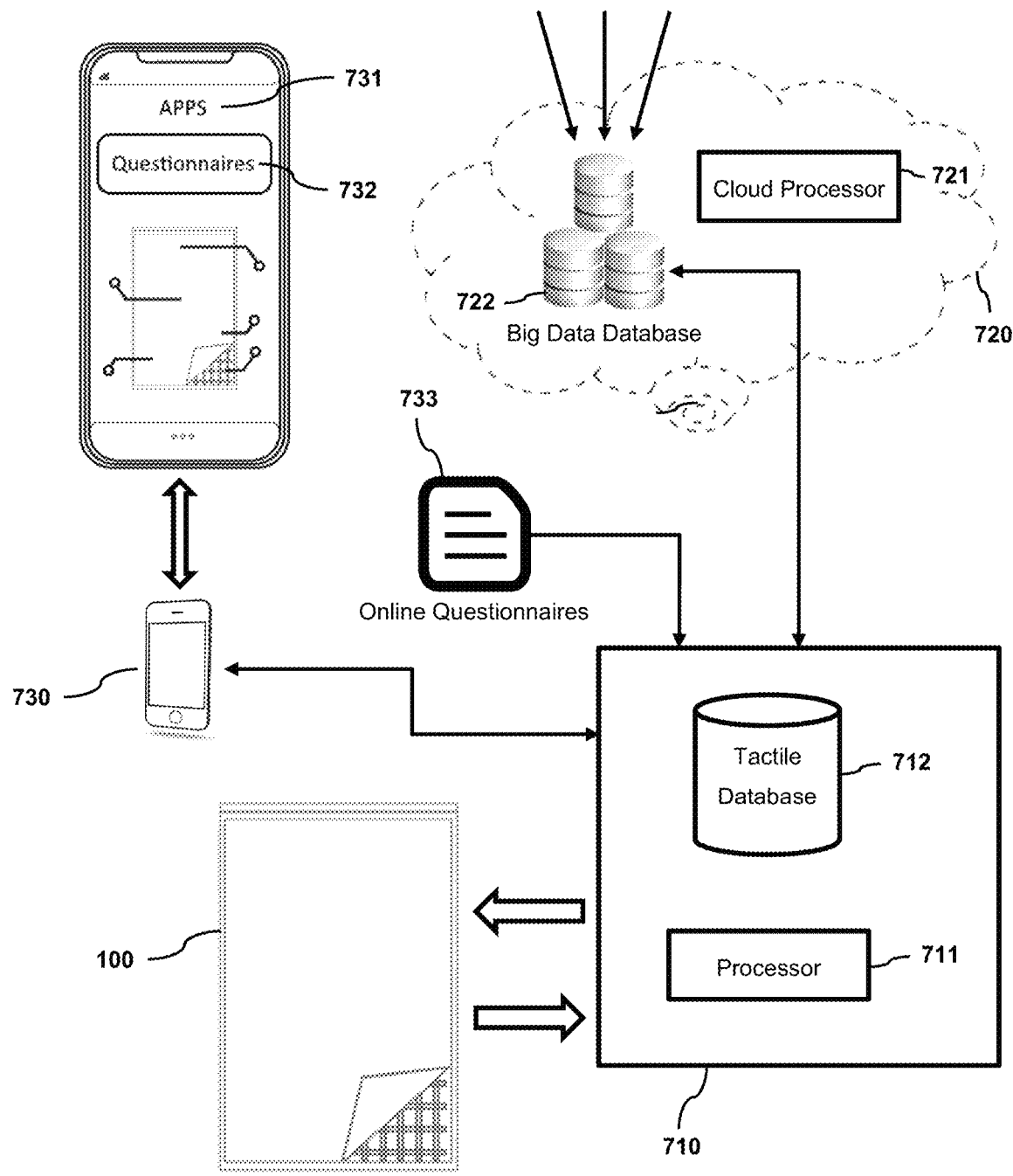
FIG. 7 depicts a block diagram of the sleeping comfort evaluation system according to certain embodiments.
Figure 8:
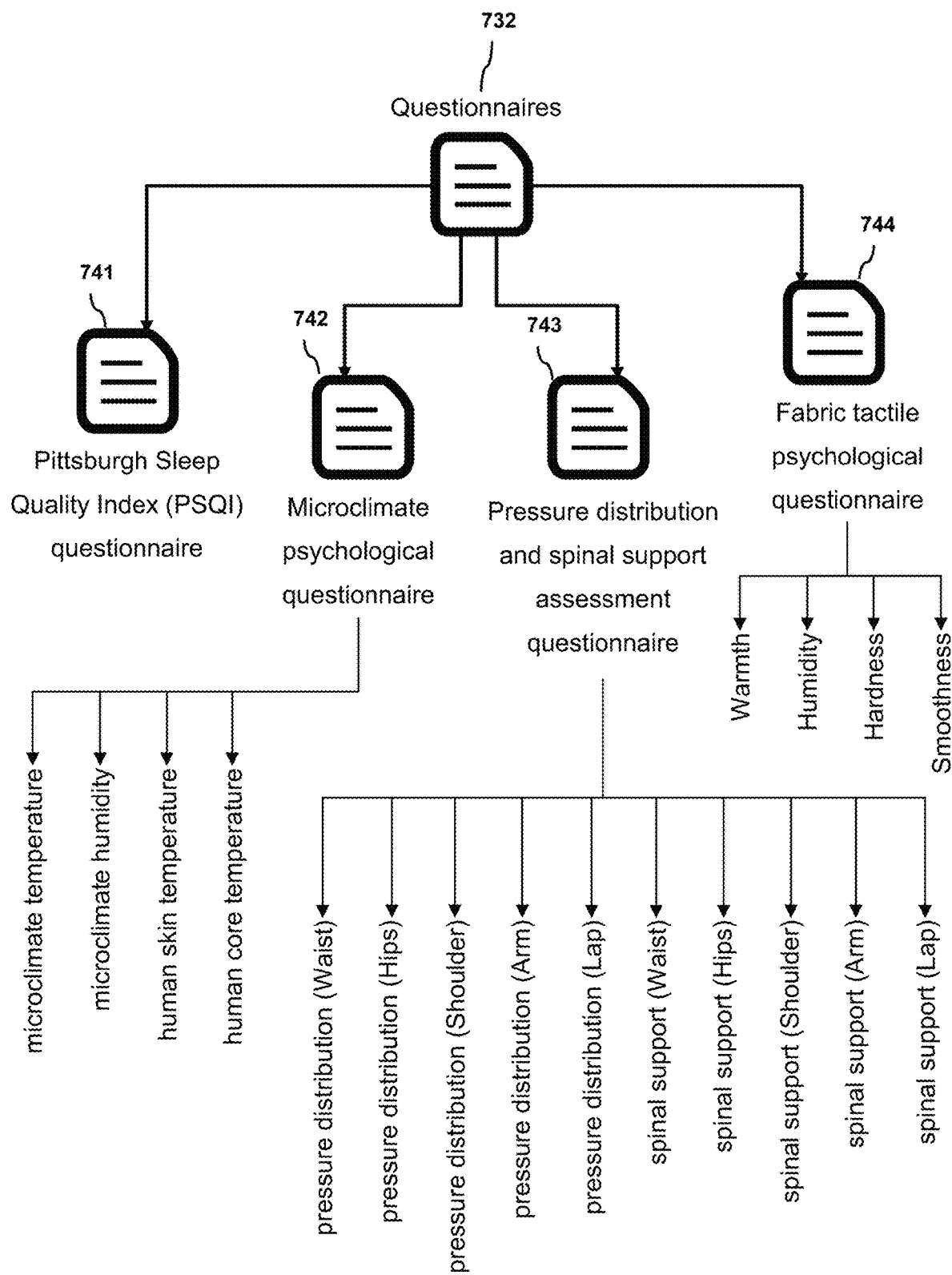
FIG. 8 depicts the plurality of questionnaires and the assessment criteria of each questionnaire according to certain embodiments.

FIG. 7 is a block diagram illustrating the sleeping comfort evaluation system in accordance with certain embodiments of the present disclosure. Particularly, a sleeping comfort evaluation system for providing real-time sleeping comfort monitoring and making adjustment on the bedding microclimate, pressure distribution, and spinal support of a bedding system is disclosed. The hardware system 100 collects real-time data using the temperature sensors 121, the humidity sensors 122, the pressure sensors 132, the spinal alignment measurement device 410, the sensors 141 of the polysomnography system 140, and the acceleration sensor 150. The real-time data recorded can be provided to the computational system 710 by wired communication method, including inter-integrated circuit ($I^2C$), serial communication, parallel communication, Universal Serial Bus (USB) communication, or other wireless communication, such as Wireless Body Area Network (WBAN) and Bluetooth. Caching techniques may also be adopted to guarantee smooth data transmission.

The computational system 710 is one or more computer devices configured to receive and process the real-time data for performing objective data analysis. The computational system 710 comprises a processor 711 and a tactile database 712. The real-time data is analyzed by the processor to obtain a real-time information with respect to the sleeping comfort performance of the bedding system. The tactile database 712 stores mechanical test results of the bed fabrics for evaluating the touch comfort of the bed fabric used in the bedding. The computational system 710 is communicatively connectable to a portable device 730 for transmitting real-time data and other data for evaluating the comfort levels of the bedding system and adjusting the hardware system 100. Therefore, the computational system 710 and the portable device 730 may include electronic circuits having data processing and communication capabilities. In some implementations, the computational system 710 and the portable device 730 may both include a processor, a memory, a power source or a battery, a communication unit, and a display. The computational system 710 and the portable device 730 may couple to and communicate with each other and/or other electronic devices via a network, wired or wireless connections (e.g., USB, Bluetooth, etc.).

The portable device 730 can be any portable electronic devices, for example: smart-phone, smart-watch, tablet, personal digital assistant (PDA), laptop, or other electronic device with one or more microcontrollers that can easily be carried along with. The mobile processor can be a processor or a computation system of the portable device 730 capable of performing computation. In one embodiment, the computation can be performed by the mobile processor and/or other cloud-based processors. A mobile application 731 is executable on the portable device 730, which is designed to provide visual summary regarding the information obtained from the hardware system 100 such that the sleeper can review the sleeping comfort evaluation results. The mobile application 731 is advantageously include a plurality of questionnaires 732 for assessing the subjective opinion of the sleeper on the thermal and moisture comfort, biomechanical comfort, touch comfort, and sleep quality. In an alternative embodiment when a portable device 730 is not used, the plurality of questionnaires can be provided as a plurality of online questionnaires 733 instead. The visualization of the sleeping comfort result can also be displayed on a designated website.

In certain embodiments, the computational system 710 is configured to communicatively connect to a cloud system 720 through a public or a private wide-area network (internet or intranet). The communication can be wired or wireless in nature, and the data transfer can take place simultaneously when receiving real-time data from the hardware system 100, or on a scheduled basis mainly when the computational system 710 is running without an internet connection.

In an exemplary implementation of the present disclosure, the cloud system 720 includes, among other things, a cloud processor 721 and a Big Data database 722. In certain embodiments, the cloud system 720 may be implemented using an intranet system accessible by designated members for uploading or downloading data in relation to the fabric handle properties of the bed fabrics to and from the Big Data database 722. Preferably, the cloud processor 721 is configured to perform computations, analysis, data management, organization, or any combination thereof. The cloud processor 721 is processed within the cloud system 720, and programmed in the format and with the syntax necessary for executing the above operations. Preferably, the cloud processor 721 has better computational power than the processor 711, which can help to offload the computationally intensive operations to the cloud processor 721. In further detail, the cloud processor 721 is configured to conduct data analysis and apply machine learning algorithm to extract useful insights from the subjective opinion obtained from the fabric tactile psychological questionnaire 744, which can be used to further update the Big Data database 722.

The Big Data database 722 stores a collection of mechanical test results of the bed fabrics and the subjective opinions thereof. Test results and subjective opinions submitted to the Big Data database 722 are generally numerical and parametrical records. Other relevant information, such as the personal demographic information, may also be included for categorizing the subjective opinions. For example, the subjective opinions can be arranged according to the gender and age groups. Opinions of similar personal demographic as the sleeper can be extracted from the Big Data database 722, and can be sent to the computational system 710 for processing.

The tactile database 712 includes data and information that can be used to evaluate the touch comfort of the bed fabrics. The data may include physical parameters obtained from objective mechanical test results of the bed fabric, including but not limited to, thermal conductivity, heat flux, bending stiffness, bending work, surface roughness, and surface friction. The sleeper may choose a desired material for the bed fabric based on the test results in the tactile database 712.

In certain embodiments, the touch comfort assessment is performed by the processor 711 by analyzing the sleeper's subjective opinion on the psychological skin tactile as collected from the fabric tactile psychological questionnaire 744. The questionnaire has the assessment criteria on the sleeper's opinion on the warmth, humidity, hardness, and smoothness of the bed fabrics, as shown in FIG. 8. The processor 711 is then configured to use regression analysis to model the objective mechanical test results in the tactile database 712 and the subjective opinion in the fabric tactile psychological questionnaire 744, thereby the relationship between the subjective opinion and the objective performance of the bed fabric can be modelled. As shown in Table I, a relationship model of the subjective opinion and the objective performance in accordance with the present disclosure is described.

TABLE 1

Relationship Model of the Subjective and Objective performance of the bed fabric

| Subjective Opinion | Objective Performance | Model |
|---|---|---|
| Warmth | Thermal Conductivity, Heat Flux | (Warmth) = 0.938 − 0.268 * (Thermal Conductivity) − 0.413 * (Heat Flux) R-value = 0.540 |
| Humidity | Thermal Conductivity, Heat Flux | (Humidity) = 0.308 + 0.269 * (Thermal Conductivity) + 0.135 * (Heat Flux) R-value = 0.859 |
| Hardness | Bending Stiffness, Bending Work | (Hardness) = 0.630 + 0.138 * (Bending Stiffness) − 0.305 * (Bending Work) R-value = 0.488 |
| Smoothness | Surface Roughness, Surface Friction | (Smoothness) = 0.841 − 0.262 * (Surface Roughness) − 0.030 * (Surface Friction) R-value = 0.652 |

As a result, the objective mechanical test results in the tactile database 712 can be used to derive the subjective fabric touch comfort in accordance with the formulas in Table I. The preferred fabric handle properties for a particular group of sleepers can be identified, which can help to meet the sleeping comfort requirement for optimizing the performance of the bedding system.

In certain embodiments, the sleep quality assessment is performed by the processor 711 by analyzing the real-time data from the sensors 141 of the polysomnography system 140. The sensors 141 can collect real-time data for evaluating assessment parameters including the total sleep time, sleep onset latency, number of awake, wake after sleep onset, deep sleep time, sleep efficiency, and number of turn over. The parameters are analyzed with the subjective opinion obtained from the PSQI questionnaire 741.

In certain embodiments, the thermal and moisture comfort assessment is performed by the processor 711 by analyzing the real-time data from the temperature sensors 121 and the humidity sensors 122. The processor 711 is configured to use the collected real-time temperature and humidity data for evaluating assessment parameters including the microclimate temperature, microclimate humidity, human skin temperature, and human core temperature. The collected data are analyzed with the subjective opinion obtained from the microclimate psychological questionnaire 742.

The microclimate psychological questionnaire 742 is designed to assess the sleeper's opinion on the microclimate temperature, microclimate humidity, human skin temperature, and human core temperature, as shown in FIG. 8. The sleeper can rank from 1 to 7 for each assessment item.

In certain embodiments, the biomechanical comfort assessment is performed by the processor 711 by analyzing the real-time data from the pressure sensors 132. The processor 711 is configured to use the collected real-time pressure data for evaluating assessment parameters including the average pressure, the maximum pressure, and the body suspension percentage. The spinal support assessment is performed by the processor 711 by analyzing the real-time data from the spinal alignment measurement device 410. The processor 711 is configured to use the collected real-time data on spinal alignment for evaluating assessment parameters including a deviation area of a back of the sleeper, a deviation angle of the back, and/or a deviation distance of the back. The collected data are analyzed with the subjective opinion obtained from the pressure distribution and spinal support assessment questionnaire 743.

The pressure distribution and spinal support assessment questionnaire 743 is designed to assess the sleeper's opinion on the pressure distributions and spinal support for the waist, hips, shoulder, arm, and lap, as shown in FIG. 8. The sleeper can rank from 1 to 7 for each assessment item of each part of the body.

In further detail, the above-mentioned assessment parameters are analyzed using radar charts. For each parameter of "Sleep Quality" and "Touch Comfort", the data is used for categorizing the performance into three standards, namely "Ideal", "Satisfied", and "Dissatisfied". For each parameter of "Thermal and Moisture Comfort" and "Biomechanical Comfort", the data is used for categorizing the performance into two standards, namely "Satisfied", and "Dissatisfied".

Figure 9:
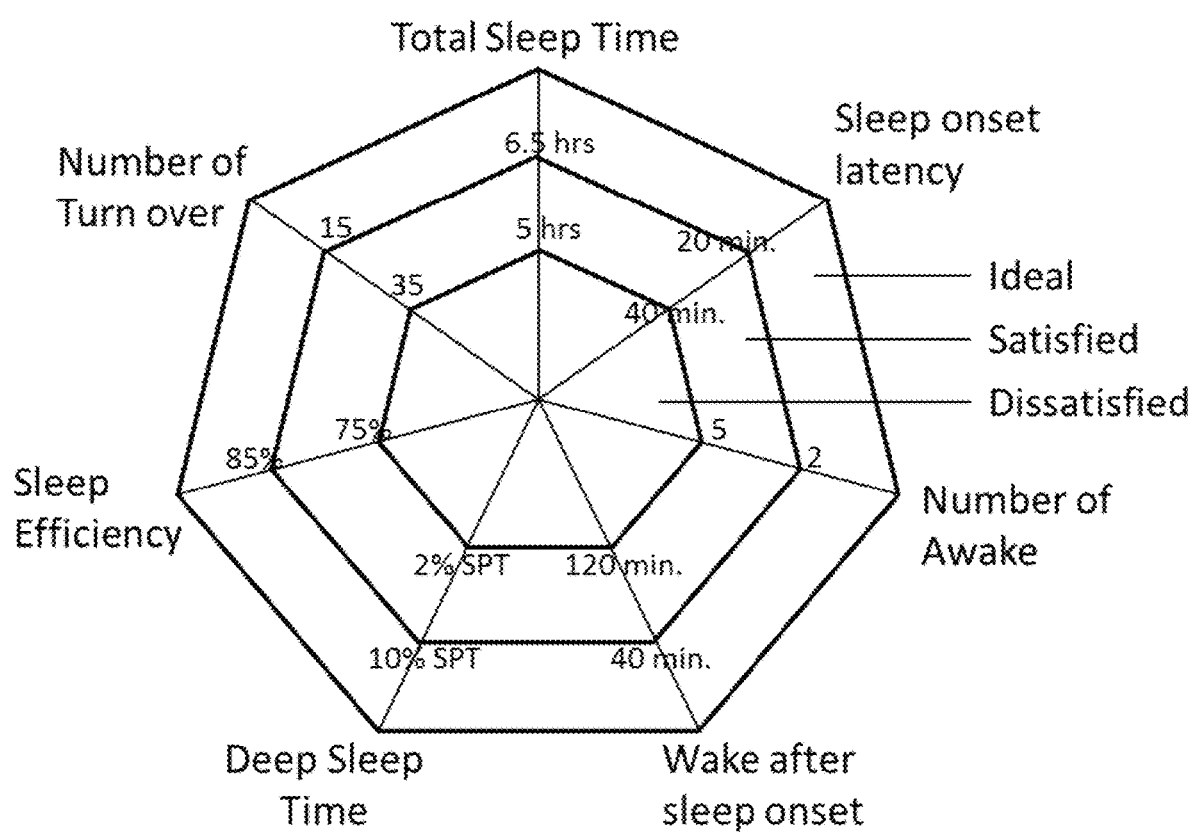
FIG. 9 is a radar chart showing the assessment parameters for the sleep quality assessment according to certain embodiments.

The assessment parameters for the sleep quality assessment are shown in the radar chart in FIG. 9. The assessment considers the total sleep time, sleep onset latency, number of awake, wake after sleep onset, deep sleep time, sleep efficiency, and number of turn over. Table II shows exemplary rules for different standards. In one embodiment, the evaluation rule for an acceptable condition is to have at least five assessment parameters rated as satisfied.

TABLE II

Classification Rules for Sleep Quality Assessment

| Parameter | Ideal | Satisfied | Dissatisfied |
|---|---|---|---|
| Total sleep time | >6.5 hours | 5-6.5 hours | <5 hours |
| Sleep onset latency | <20 minutes | 20-40 minutes | >40 minutes |
| Number of awake | 0-1 times | 2-5 times | 6 times or more |
| Wake after sleep onset | <40 minutes | 40-120 minutes | >120 minutes |
| Deep sleep time (% sleep period time) | >10% sleep period time | 2-10% sleep period time | 0-1% sleep period time |
| Sleep efficiency | >85% | 75-85% | <75% |
| Number of turn over | <15 | 15-35 | >35 |

Figure 10:
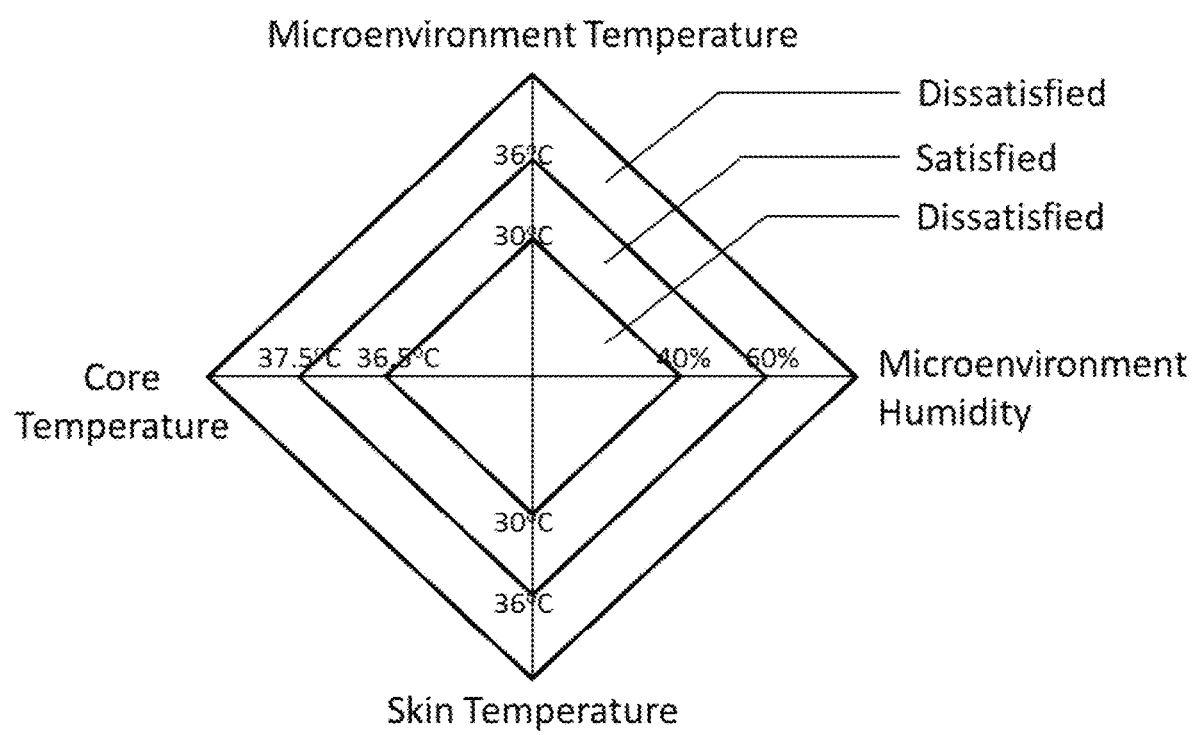
FIG. 10 is a radar chart showing the assessment parameters for the thermal and moisture comfort assessment according to certain embodiments.

The assessment parameters for the thermal and moisture comfort assessment are shown in the radar chart in FIG. 10. The assessment considers the microclimate temperature, microclimate humidity, human skin temperature, and human core temperature. Table III shows exemplary rules for different standards. In one embodiment, the evaluation rule for an acceptable condition is to have at least three assessment parameters rated as satisfied.

TABLE III

Classification Rules for Thermal and Moisture Comfort Assessment

| Parameters | Satisfied | Dissatisfied |
|---|---|---|
| Microclimate temperature | 30-36° C. | <30° C. or >36° C. |
| Microclimate humidity | 40-60% RH | <40% RH or >60% RH |
| Human skin temperature | 30-36° C. | <30° C. or >36° C. |

TABLE III-continued

Classification Rules for Thermal and Moisture Comfort Assessment

| Parameters | Satisfied | Dissatisfied |
|---|---|---|
| Human core temperature | 36.5-37.5° C. | <36.5° C. or >37.5° C. |

Figure 11:
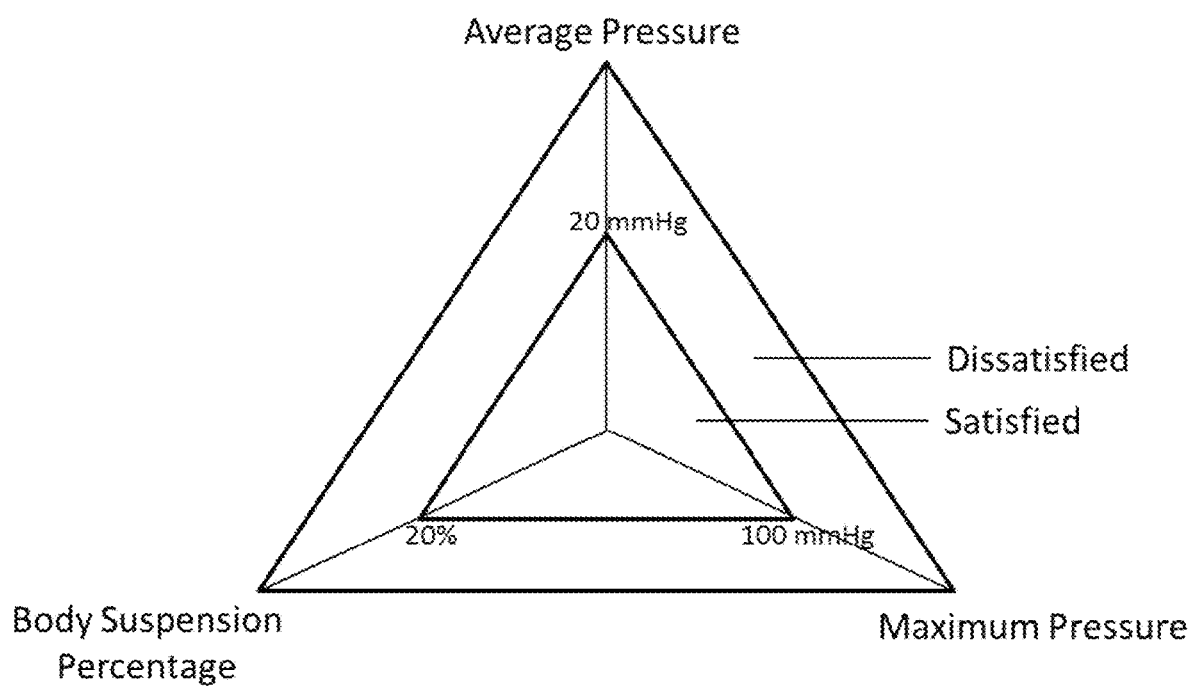
FIG. 11 is a radar chart showing the assessment parameters for the biomechanical comfort assessment according to certain embodiments.

The assessment parameters for the biomechanical comfort assessment are shown in the radar chart in FIG. 11. The assessment considers the average pressure, the maximum pressure, and the body suspension percentage. Table IV shows exemplary rules for different standards. In one embodiment, the evaluation rule for an acceptable condition is to have at least two assessment parameters rated as satisfied.

TABLE IV

Classification Rules for Biomechanical Comfort Assessment

| Parameters | Satisfied | Dissatisfied |
|---|---|---|
| Average pressure | <20 mmHg | >20 mmHg |
| Maximum pressure | <100 mmHg | >100 mmHg |
| Body suspension percentage | <20% | >20% |

Figure 12:
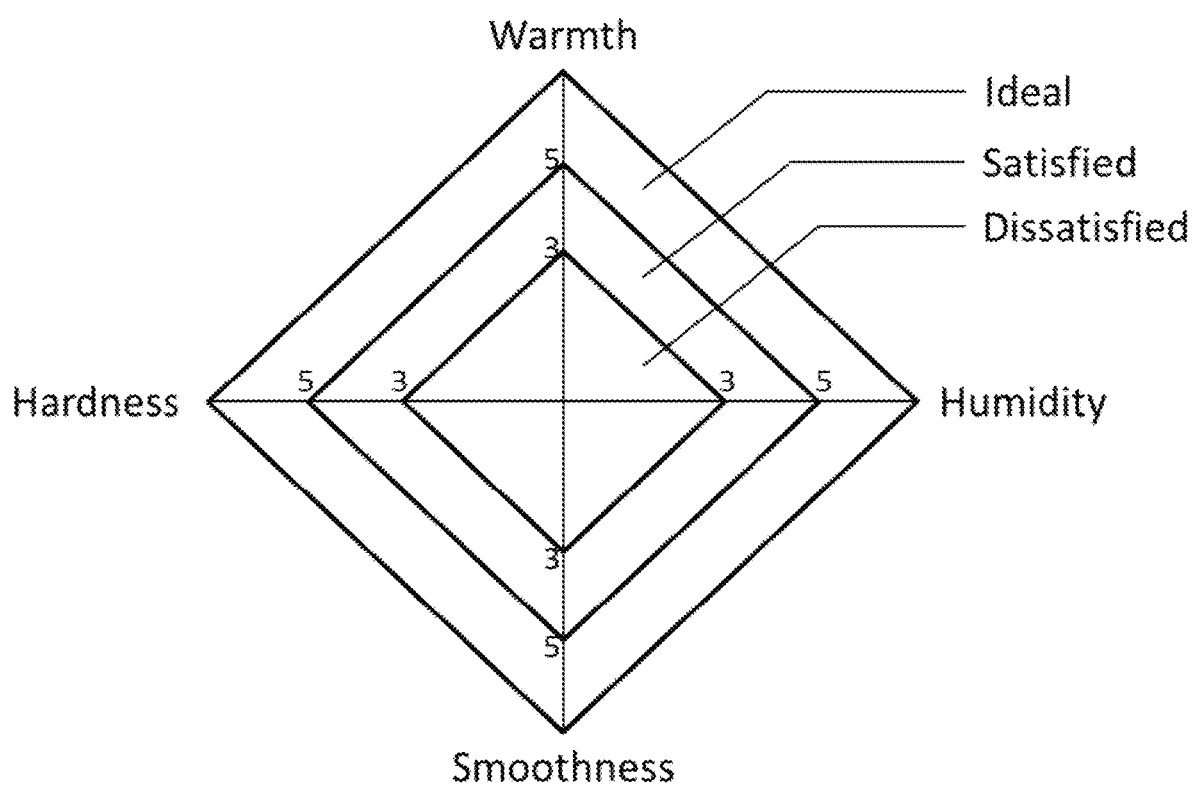
FIG. 12 is a radar chart showing the assessment parameters for the touch comfort assessment according to certain embodiments.

The assessment criteria for the touch comfort assessment are shown in the radar chart in FIG. 12. The assessment allows the sleeper to rank the warmth, humidity, hardness, and smoothness of the bed fabrics. Table V shows exemplary rules for different standards. In one embodiment, the evaluation rule for an acceptable condition is to have at least three assessment criteria rated as satisfied.

TABLE V

Classification Rules for Touch Comfort Assessment

| Criteria | Ideal | Satisfied | Dissatisfied |
|---|---|---|---|
| Warmth | 6-7 | 3-5 | 0-2 |
| Humidity | 6-7 | 3-5 | 0-2 |
| Hardness | 6-7 | 3-5 | 0-2 |
| Smoothness | 6-7 | 3-5 | 0-2 |

In certain embodiments, knowledge can be extracted from the plurality of questionnaires 732 having the subjective opinion of the sleeper on the thermal and moisture comfort, biomechanical comfort, touch comfort, and sleep quality, which can be used to uncover hidden patterns, correlations and other insights. Therefore, with the consent of the sleeper, the knowledge can be uploaded to the Big Data database 722 for improving the accuracy of the optimization for the bedding system.

The assessment results for the thermal and moisture comfort, biomechanical comfort, touch comfort, and sleep quality can also be used by the computational system 710 for evaluating the bedding comfort levels and adjusting the hardware system 100. Advantageously, the present disclosure allows a combined analysis of the subjective and objective performance of the bedding system. If the assessment result is found to be unsatisfactory, the processor 711 is configured to send instructions to the hardware system 100, and control the thermal and moisture comfort control system 200 for adjusting the one or more bedding temperature of the bedding and the one or more bedding relative humidity, and the mattress firmness control machine 302 for adjusting the firmness of each firmness-controllable component mattress.

Trial Test Results

The performance of the sleeping comfort evaluation system in accordance with the present disclosure was evaluated under trial tests.

In the first trip test, a participant without sleep disorder was invited to take the test. The sleep health was evaluated according to the PSQI questionnaire 741, with a PSQI<5 score (healthy).

Next, the temperature sensors 121, the humidity sensors 122, the sensors 141 of the polysomnography system 140, and the acceleration sensor 150 suitably placed for collecting the physiological data. The thermal and moisture comfort control system can control the temperature of the bedding to 32-34° C., and the relative humidity to 40-80%. The bedding used has five firmness-controllable component mattresses 303, controllable by the mattress firmness control machine 302. The bed fabric is selected from the tactile database 712 with a tactile performance score of 6-7. Theoretically, the bedding system integrating the optimization in thermal comfort, biomechanics comfort, and touch comfort should achieve a comfortable state.

The participant was instructed to perform a sleep test for 570 minutes (including a rest of 30 minutes before sleep and the time for completing the questionnaires), with the real-time data in relation to the physical parameters of the bedding system and the physiological changes of the participant. After the sleep test, the participant was instructed to complete the plurality of questionnaires 732. Table VI summarizes the results:

TABLE VI

Summary of the Frist Trial Test

| Total sleep time | Sleep onset latency | Number of awake | Wake after sleep onset | Deep sleep time (%) | Sleep efficiency | Number of turn over |
| --- | --- | --- | --- | --- | --- | --- |
| 8.1 hours | 6 minutes | 1 time | 15 minutes | 10% | 87% | 3 times |

| Microclimate temperature | Microclimate humidity | Human Skin temperature | Human core temperature |
| --- | --- | --- | --- |
| 30° C. | 79% | 30° C. | 37.4° C. |

| Average pressure | Maximum pressure | Body suspension percentage |
| --- | --- | --- |
| 9.2 mmHg | 35 mmHg | 7% |

TABLE VI-continued

Summary of the Frist Trial Test

| Warmth | Humidity | Hardness | Smoothness |
| --- | --- | --- | --- |
| 5 | 6 | 7 | 2 |

The final results show that the sleep quality and sleeping comfort performance of the bedding system are satisfactory.

In the second trial test, the temperature of the bedding is controlled to 23° C. and the relative humidity is set to 85%. The mattress is also changed to another one that is harder. Table VII below summarizes the results:

TABLE VII

Summary of the Second Trial Test

| Total sleep time | Sleep onset latency | Number of awake | Wake after sleep onset | Deep sleep time (%) | Sleep efficiency | Number of turn over |
| --- | --- | --- | --- | --- | --- | --- |
| 5.7 hours | 17.5 minutes | 7 times | 116 minutes | 1.3% | 71% | 38 times |

| Microclimate temperature | Microclimate humidity | Human Skin temperature | Human core temperature |
| --- | --- | --- | --- |
| 28.7° C. | 82% | 29.8° C. | 36.6° C. |

| Average pressure | Maximum pressure | Body suspension percentage |
| --- | --- | --- |
| 19.4 mmHg | 162 mmHg | 23.6% |

| Warmth | Humidity | Hardness | Smoothness |
| --- | --- | --- | --- |
| 0 | 1 | 2 | 4 |

The final results show that the sleep quality and sleeping comfort performance of the bedding system are unsatisfactory.

This illustrates the fundamental sleeping comfort evaluation system having a hardware system and a software system for providing real-time sleeping comfort evaluation of a bedding in accordance with the present disclosure. It will be apparent that variants of the above-disclosed and other features and functions, or alternatives thereof, may be combined into many other different methods or apparatuses. The present embodiment is, therefore, to be considered in all respects as illustrative and not restrictive. The scope of the disclosure is indicated by the appended claims rather than by the preceding description, and all changes that come within the meaning and range of equivalency of the claims are therefore intended to be embraced therein.

What is claimed is:

1. An evaluation system for evaluating sleeping comfort performance of a bedding system, the evaluation system comprising:
 a computational system having a processor and a tactile database comprising data and information in relation to objective mechanical test results of bed fabrics for evaluating a touch comfort of the bed fabrics of the bedding;
 a portable device; and
 a hardware system for collecting real-time data, the hardware system comprising:
 a thermal and moisture comfort measurement system comprising a plurality of first temperature sensors and a plurality of humidity sensors, each first temperature sensor being used for measuring a temperature of a position of a bedding, each humidity sensor being used for measuring a relative humidity of a position of the bedding;

a thermal and moisture comfort control system for adjusting one or more bedding temperatures of the bedding and one or more bedding relative humidity of the bedding;

a biomechanical comfort control system comprising a firmness-controllable mattress and a mattress firmness control machine, the firmness-controllable mattress comprising a plurality of firmness-controllable component mattresses, the mattress firmness control machine being used for adjusting firmness of each firmness-controllable component mattress such that pressure distribution on an interface between a sleeper and the firmness-controllable mattress and a spinal alignment of the sleeper is adjustable; and a biomechanical comfort measurement system comprising a pressure sensing mat and a spinal alignment measurement device, the pressure sensing mat being located on the firmness-controllable mattress and comprising a plurality of pressure sensors, each pressure sensor being used for measuring pressure on a position of the interface such that the pressure distribution on the interface is obtained based on the measured pressure, the spinal alignment measurement device being used for measuring one or more spinal alignment parameters of the sleeper, wherein:

the computational system is configured to receive and process the real-time data from the hardware system, and is communicatively connected to the portable device for transmitting the real-time data for evaluating the bedding system and adjusting the hardware system;

a mobile application executable on the portable device is configured to collect subjective opinion of the sleeper using a plurality of questionnaires; and the processor is configured to perform combined analysis of the subjective opinion and the real-time data of the bedding system, and send instructions to the hardware system to:

control the thermal and moisture comfort control system for adjusting the one or more bedding temperature of the bedding and the one or more bedding relative humidity; and control the mattress firmness control machine for adjusting the firmness of each firmness-controllable component mattress.

2. The evaluation system of claim 1, wherein the thermal and moisture comfort measurement system further comprises a second temperature sensor and a second humidity sensor, the second temperature sensor being used for measuring an ambient temperature, the second humidity sensor being used for measuring an ambient relative humidity.

3. The evaluation system of claim 1, wherein the thermal and moisture comfort measurement system further comprises a plurality of third temperature sensors, each third temperature sensor being used for measuring a skin temperature of a part of the sleeper.

4. The evaluation system of claim 1, wherein the spinal alignment measurement device comprises a laser liner and a plurality of stickers, the plurality of stickers being used for being attached on a back of the sleeper, the laser liner being used for detecting a position of each sticker.

5. The evaluation system of claim 1, wherein the spinal alignment measurement device comprises a camera for capturing images of the back of the sleeper.

6. The evaluation system of claim 1, wherein the one or more spinal alignment parameters include a deviation area of a back of the sleeper, a deviation angle of the back and/or a deviation distance of the back.

7. The evaluation system of claim 1 further comprising a bed, wherein the firmness-controllable mattress is located on the bed; and the thermal and moisture comfort control system comprises a temperature and humidity regulator, a blower, a tube and a plurality of diffuser plates, the tube connecting the temperature and humidity regulator and the blower, the blower being used for generating an airflow to the bed via the plurality of diffuser plates, the temperature and humidity regulator being used for adjusting a temperature of the air flow and a relative humidity of the air flow such that the one or more bedding temperatures and the one or more bedding relative humidity are adjusted.

8. The evaluation system of claim 1, wherein the bedding has a plurality of microclimate controllable zones, the bedding temperature and the bedding relative humidity in each microclimate controllable zone are adjusted individually by the thermal and moisture comfort control system.

9. The evaluation system of claim 1, wherein each firmness-controllable component mattress comprises a bag; and the mattress firmness control machine comprises a pump for pumping air or a liquid into or out of the bag of each firmness-controllable component mattress.

10. The evaluation system of claim 1, wherein the plurality of firmness-controllable component mattresses has three firmness-controllable component mattresses, five firmness-controllable component mattresses or seven firmness-controllable component mattresses.

11. The evaluation system of claim 1, wherein the hardware system further comprises a polysomnography system for measuring one or more physiological parameters of the sleeper.

12. The evaluation system of claim 1, wherein the hardware system further comprises an acceleration sensor for determining position changes of the sleeper.

13. The evaluation system of claim 1, wherein the objective mechanical test results comprise thermal conductivity, heat flux, bending stiffness, bending work, surface roughness, and surface friction of the bed fabrics.

14. The evaluation system of claim 1, wherein the processor is configured to use regression analysis to model a relationship between the objective mechanical test results of the bed fabrics and the subjective opinion.

15. The evaluation system of claim 1, wherein the processor is further configured to:

control the thermal and moisture comfort control system based on the real-time data measured by thermal and moisture comfort measurement system; and control the biomechanical comfort control system based on the real-time data measured by the biomechanical comfort measurement system.

16. An evaluation system for evaluating sleeping comfort performance of a bedding system, the evaluation system comprising:

a portable device; and a hardware system comprising:

a thermal and moisture comfort control system for adjusting one or more bedding temperatures of a bedding and one or more bedding relative humidity of the bedding; and a biomechanical comfort control system comprising a firmness-controllable mattress and a mattress firmness control machine, the firmness-controllable mattress comprising a plurality of firmness-controllable component mattresses, the mattress firmness control machine being used for adjusting firmness of each firmness-controllable component mattress such that pressure distribution on an interface between a sleeper and the firmness-controllable mattress and the spinal alignment of the sleeper are adjustable;

wherein:
a mobile application executable on the portable device is configured to collect subjective opinion of the sleeper using a plurality of questionnaires, wherein the plurality of questionnaires comprises a Pittsburgh Sleep Quality Index (PSQI) questionnaire, a microclimate psychological questionnaire, a pressure distribution and spinal support assessment questionnaire, and a fabric tactile psychological questionnaire.

17. An evaluation system for evaluating sleeping comfort performance of a bedding system, the evaluation system comprising:
a computational system having a tactile database comprising data and information in relation to objective mechanical test results of bed fabrics for evaluating a touch comfort of the bed fabrics of the bedding;
a portable device;
a cloud system comprising a cloud processor and a Big Data database of bed fabrics; and
a hardware system for collecting real-time data, the hardware system comprising:
a thermal and moisture comfort measurement system comprising a plurality of first temperature sensors and a plurality of humidity sensors, each first temperature sensor being used for measuring a temperature of a position of a bedding, each humidity sensor being used for measuring a relative humidity of a position of the bedding;
a biomechanical comfort measurement system comprising a pressure sensing mat and a spinal alignment measurement device, the pressure sensing mat comprising a plurality of pressure sensors, each pressure sensor being used for measuring pressure on a position of an interface such that pressure distribution on the interface is obtained based on the measured pressure, the spinal alignment measurement device being used for measuring one or more spinal alignment parameters of the sleeper, wherein:
the computational system is configured to receive and process the real-time data from the hardware system, and is communicatively connected to the portable device for transmitting real-time data for evaluating the bedding system and adjusting the hardware system;
a mobile application executable on the portable device is configured to collect subjective opinion of a sleeper using a plurality of questionnaires;
the Big Data database stores a collection of mechanical test results of the bed fabrics and the subjective opinions of the bed fabrics; and
the subjective opinions are categorized according to personal demographic information enabling an extraction of relevant information from the Big Data database.

* * * * *